United States Patent [19]
Hedenstrom et al.

[11] Patent Number: 6,132,760
[45] Date of Patent: Oct. 17, 2000

[54] TRANSDERMAL DEVICE FOR THE DELIVERY OF TESTOSTERONE

[75] Inventors: John C. Hedenstrom, St. Paul; Michael L. Husberg, West St. Paul; Shari L. Wilking, Inver Grove Heights; Matthew T. Scholz, Woodbury, all of Minn.

[73] Assignee: 3M Innovative Properties Company, St. Paul, Minn.

[21] Appl. No.: 09/031,619

[22] Filed: Feb. 27, 1998

Related U.S. Application Data

[60] Provisional application No. 60/039,274, Feb. 28, 1997.

[51] Int. Cl.⁷ .............................. A61F 13/02; A61F 13/00
[52] U.S. Cl. ............................. 424/448; 424/449
[58] Field of Search ..................... 424/448, 449

[56] References Cited

U.S. PATENT DOCUMENTS

| | | | |
|---|---|---|---|
| 5,079,008 | 1/1992 | Sinnreich | 424/448 |
| 5,152,997 | 10/1992 | Ebert et al. | 424/449 |
| 5,164,190 | 11/1992 | Patel et al. | 424/448 |
| 5,211,952 | 5/1993 | Spicer et al. | 424/426 |
| 5,230,897 | 7/1993 | Griffin et al. | 424/449 |
| 5,240,932 | 8/1993 | Morimoto et al. | 514/282 |
| 5,340,586 | 8/1994 | Pike et al. | 424/426 |
| 5,460,820 | 10/1995 | Ebert et al. | 424/449 |
| 5,676,968 | 10/1997 | Lipp | 424/448 |
| 5,679,373 | 10/1997 | Wick | 424/448 |
| 5,866,157 | 2/1999 | Higo | 424/448 |

FOREIGN PATENT DOCUMENTS

| | | |
|---|---|---|
| 0 491 076 A1 | 6/1992 | European Pat. Off. . |
| 0 563 507 1 | 10/1993 | European Pat. Off. . |
| 42 10 165 A 1 | 2/1993 | Germany . |
| WO 91/05529 | 5/1991 | WIPO . |

OTHER PUBLICATIONS

Misra et al "Biphasic Testosterone Delivery Profile Observed wth Two Different Transdermal Formulations" *Pharmaceutical Research*, 1997 vol. 14, No. 9, pp. No. 1264–1268.

Loftsson et al, "Cyclodextrins as Co–enhancers in Dermal and Transdermal Drug Delivery," *Pharmazie*, 1998, vol. 53 (2), pp. No. 137–139.

Article entitled The enhancement index concept applied to terpene penetration enhancers for human skin and model lipophilic (oestradiol) and hydrophilic (5–fluorouracil) drugs, by A.C. Williams and B.W. Barry, from the International Journal of Pharmaceutics, 74 (1991), pp. 157–168.

*Primary Examiner*—Thurman K. Page
*Assistant Examiner*—Todd D Ware
*Attorney, Agent, or Firm*—MarySusan Howard; Ted K. Ringsred; Robert W. Sprague

[57] ABSTRACT

A transdermal delivery device including an adhesive layer that contains a therapeutically effective amount of testosterone and a delivery enhancing adjuvant comprising a terpene.

20 Claims, No Drawings

TRANSDERMAL DEVICE FOR THE DELIVERY OF TESTOSTERONE

This application is a continuation of Ser. No. 60/039,274, filed Feb. 28, 1997, which is incorporated herein by reference.

FIELD OF THE INVENTION

The present invention relates to transdermal drug delivery devices. In another aspect this invention relates to pharmaceutical formulations containing testosterone.

BACKGROUND OF THE INVENTION

Transdermal drug delivery devices are designed to deliver a therapeutically effective amount of drug across the skin of a patient. Devices known to the art include reservoir type devices involving membranes that control the rate of drug release to the skin and devices involving a dispersion of the drug in a matrix such as a pressure sensitive adhesive. The skin, however, presents a substantial barrier to ingress of foreign substances into the body. It is therefore often desirable or necessary to incorporate certain materials that enhance the rate at which the drug passes through the skin. However, the type of device, the transdermal flux rate that is suitable, and the suitable formulation components are dependent upon the particular drug to be delivered.

Testosterone is the main androgenic hormone formed in the testes. Testosterone therapy is currently indicated for the treatment of male hypogonadism. It is also under investigation for the treatment of wasting conditions associated with AIDS and cancer, testosterone replacement in men over the age of 60, osteoporosis, combination hormone replacement therapy for women and male fertility control.

In recent years there has been interest in developing a useful method of delivering testosterone transdermally to both men and women. Ebert et al., U.S. Pat. No. 5,152,997, describes a device for the transdermal delivery of testosterone that contains testosterone in a matrix that additionally includes a penetration enhancer. In U.S. Pat. No. 5,460,820 Ebert et al. describe a device for providing testosterone replacement therapy to women that delivers 50 to 500 µg/day testosterone to the woman. The '820 devices may also include an estrogenic compound, thereby providing combination hormone replacement therapy. Pike et al., U.S. Pat. No. 5,340,586 also describes compositions that can be used to provide estrogens and androgens to women in amounts effective to prevent the symptoms of loss of ovarian function.

SUMMARY OF THE INVENTION

The present invention provides a device for the transdermal delivery of testosterone. This device comprises a backing having an adhesive layer adhered to one surface of the backing, said adhesive layer comprising:

(a) a pressure sensitive skin adhesive;

(b) a therapeutically effective amount of testosterone and (c) a delivery enhancing adjuvant comprising a terpene.

The device of the invention is able to deliver a therapeutically effective amount of testosterone to a subject. Accordingly, the invention also provides a method of treating a condition associated with testosterone deficiency in a mammal comprising the steps of providing a device for the transdermal delivery of testosterone comprising a backing having an adhesive layer adhered to one surface of the backing, said adhesive layer comprising:

(a) a pressure sensitive skin adhesive;

(b) a therapeutically effective amount of testosterone; and (c) a delivery enhancing adjuvant comprising a terpene; applying the device to the skin of a mammal; and allowing the device to remain on the skin for a time sufficient to establish or maintain a therapeutically effective blood level of testosterone in the mammal.

DETAILED DESCRIPTION OF THE INVENTION

The present invention provides transdermal drug delivery devices containing testosterone. The testosterone is present in the adhesive layer in a therapeutically effective amount, i.e., an amount effective to allow the device to deliver sufficient testosterone to achieve a desired therapeutic result in the treatment of a condition. The amount that constitutes a therapeutically effective amount varies according to the condition being treated (e.g. hypogonadism in males, testosterone deficiency in women, wasting in AIDS patients, etc.), any drugs being coadministered with testosterone, desired duration of treatment, the surface area and location of the skin over which the device is to be placed, and the selection of adjuvant and other components of the transdermal delivery device. Accordingly, it is not practical to enumerate particular preferred amounts but such can be readily determined by those skilled in the art with due consideration of these and other appropriate factors. Generally, however, testosterone is present in the adhesive layer in an amount of about 2 to about 9 percent, preferably about 2.5 to about 6.5 percent, by weight based on the total weight of the adhesive layer. A device of the invention preferably contains a therapeutically effective amount of testosterone dissolved in the adhesive layer. In a more preferred embodiment the adhesive layer is substantially free of solid undissolved testosterone, and in a particularly preferred embodiment the adhesive layer contains no solid undissolved testosterone.

The adhesive layer of the device of the invention also comprises one or more polymers, typically one or more copolymers. The polymer(s) utilized in the practice of the invention should be substantially chemically inert to testosterone, and is preferably a pressure sensitive skin adhesive. Examples of suitable types of adhesives include acrylates, natural and synthetic rubbers, polysiloxanes, polyurethanes, and other pressure sensitive skin adhesives known in the art, either alone or in combination. Preferably the adhesive is an acrylate copolymer.

The inherent viscosity of the copolymer is such as to ultimately provide a suitable pressure sensitive adhesive when used in a device of the invention. Preferably the copolymer has an inherent viscosity in the range of 0.2 dl/g to about 2 dl/g, more preferably 0.3 dl/g to about 1.4 dl/g.

Suitable copolymers for use in an adhesive layer preferably comprise about 45 to about 95 percent by weight, more preferably, 55 to 95 percent by weight, based on the total weight of all monomers in the copolymer, of one or more A monomers selected from the group consisting of alkyl acrylates containing 4 to 10 carbon atoms in the alkyl group and alkyl methacrylates containing 4 to 10 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylates and methacrylates. Preferred alkyl acrylates include isooctyl acrylate, 2-ethylhexyl acrylate, n-butyl acrylate, and cyclohexyl acrylate. The most preferred alkyl acrylate is isooctyl acrylate.

The copolymer component of the adhesive layer further comprises about 5 to about 55 percent by weight, more preferably, about 5 to about 40 percent by weight, based on the total weight of all monomers in the copolymer, of one or more B monomers. Suitable B monomers include those comprising a functional group selected from the group consisting of carboxylic acid, sulfonamide, urea, carbamate, carboxamide, hydroxy, amino, oxy, oxo, and cyano. Exemplary B monomers include acrylic acid, methacrylic acid, maleic acid, a hydroxylalkyl acrylate containing 2 to 4 carbon atoms in the hydroxyalkyl group, a hydroxyalkyl methacrylate containing 2 to 4 carbon atoms in the hydroxyalkyl group, acrylamide, methacrylamide, an alkyl substituted acrylamide containing 1 to 8 carbon atoms in the alkyl group, N-vinyl-N-methyl acetamide, N-vinyl valerolactam, N-vinyl caprolactam, N-vinyl-2-pyrrolidone, glycidyl methacrylate, vinyl acetate, alkoxyethyl acrylate containing 1 to 4 carbon atoms in the alkoxy group, alkoxyethyl methacrylate containing 1 to 4 carbon atoms in the alkoxy group, 2-ethoxyethoxyethyl acrylate, furfuryl acrylate, furfuryl methacrylate, tetrahydrofurfuryl acrylate, tetrahydrofurfuryl methacrylate, propylene glycol monomethacrylate, propylene oxide methyl ether acrylate, di(lower)alkylamino ethyl acrylate, di(lower)alkylamino ethyl methacrylate, di(lower alkyl)aminopropyl methacrylamide, acrylonitrile, and methacrylonitrile. Preferred B monomers include acrylic acid, methacrylic acid, acrylamide, methacrylamide, and vinyl acetate.

The copolymer may optionally further comprise a substantially linear macromonomer copolymerizable with the A and B monomers and having a molecular weight in the range 500–500,000, preferably 2,000–1,000,000 and more preferably, 5,000–30,000. The macromonomer, when used, is generally present in an amount of not more than about 20%, preferably not more than about 10% by weight based on the total weight of all monomers in the copolymer. Suitable macromonomers include polymethylmethacrylate, styrene/acrylonitrile, polyether and polystyrene macromonomers. Examples of useful macromonomers and their preparation are described in Krampe et al., U.S. Pat. No. 4,693,776, the disclosure of which is incorporated herein by reference.

The copolymers described above can be prepared by methods well known to those skilled in the art and described for example, in U.S. Pat. No. RE 24,906 (Ulrich), U.S. Pat. No. 4,732,808 (Krampe), and International Publication Number WO 96/08229 (Garbe), the disclosures of which are incorporated herein by reference.

If desired, the adhesive layer can contain components that modify the properties of the adhesive polymer, such as plasticizers, tackifiers, and the like.

The adhesive layer of the invention further comprises an adjuvant that enhances the transdermal delivery of testosterone. Any adjuvant that enhances the transdermal delivery of testosterone may be used in the device of the invention regardless of the way in which such enhancement is achieved. It has been found that the terpenes are an especially suitable class of enhancers, as they help to solubilize the testosterone in the adhesive as well as enhance the delivery of testosterone. Useful terpenes include pinene, d-limonene, carene, terpineol, terpinen-4-ol, carveol, carvone, pulegone, piperitone, menthone, menthol, neomenthol, thymol, camphor, borneol, citral, ionone, and cineole, alone or in any combination. Of these, terpineol, particularly α-terpineol, is preferred.

The adhesive layer may contain delivery enhancing adjuvants in addition to the terpene. These additional delivery enhancing adjuvants include, but are not limited to, alcohols; $C_{6-36}$, preferably $C_{8-20}$ fatty acids, esters, alcohols and amides; and alkyl pyrrolidone carboxylates having alkyl groups containing from 6 to 36 carbon atoms, preferably 8 to 20 carbon atoms.

Preferred delivery enhancing adjuvants include lauryl alcohol, lauramide DEA, lauryl pyrrolidone-5-carboxylate (e.g. Laurydone®); ascorbyl palmitate; glycerol; tetraglycol (α-[(tetrahydro-2-furanyl)methyl]-ω-hydroxy-poly(oxy-1, 2-ethanediyl)), lauryl glycol (i.e. 1,2-dodecanediol) and mixtures thereof.

In a device of the invention the adjuvant(s) is dispersed, preferably substantially uniformly, and more preferably dissolved in the adhesive and is present in an amount that enhances testosterone penetration through the skin compared to a like device not containing the adjuvant(s) when this phenomenon is measured using the skin penetration model described below. The total amount of delivery enhancing adjuvant will generally be about 20 to about 40 percent by weight based on the total weight of the adhesive layer.

The adhesive layer optionally further comprises a skin penetration enhancing amount of lauramine oxide (N,N-dimethyl-dodecanamine-N-oxide). When the adhesive layer contains lauramine oxide it will generally by present in an amount of about 1 to about 4 percent by weight based on the total weight of the adhesive layer.

Further conventional components, such as crystallization inhibitors (e.g. polyvinylpyrrolidone), can be incorporated into the adhesive layer if necessary or desirable.

In certain preferred embodiments of the invention, the amounts of excipients and testosterone are selected such that the testosterone is completely dissolved in the adhesive layer and the device provides a relatively high flux rate through the skin. In one preferred embodiment of the invention, the adjuvant comprises a mixture of terpineol, tetraglycol and lauryl glycol each present an amount of about 5 to about 15 percent, preferably about 7 to about 11 percent, by weight based on the total weight of the adhesive layer. Preferably the total amount by weight of adjuvant is about 25 to about 35 percent based on the total weight of the adhesive layer. In this embodiment, testosterone is present in the adhesive layer in an amount of about 3 to about 6 percent, preferably about 3.5 to about 4.5 percent, by weight based on the total weight of the adhesive layer.

In another preferred embodiment of the invention the adhesive layer comprises terpineol present in an amount of about 20 to about 30 percent by weight based on the total weight of the adhesive layer and lauramine oxide present in an amount of about 1 to about 4 percent by weight based on the total weight of the adhesive layer. In this embodiment, testosterone is present in the adhesive layer in an amount of about 5 to about 9 percent, preferably about 5.5 to about 6.5 percent, by weight based on the total weight of the adhesive layer.

In yet another preferred embodiment of the invention the adhesive layer comprises about 15 to 25 weight percent terpineol; about 3 to 10 weight percent lauryl alcohol; about 1 to 6 weight percent glycerol; and about 1 to 6 weight percent lauryl pyrrolidone-5-carboxylate, based on the total weight of the adhesive layer.

The properties desirable in a transdermal device are well known to those skilled in the art. For example, it is desirable to have sufficiently little cold flow that a device of the invention is stable to flow upon storage. It is also preferred that it adhere well to the skin and release cleanly from the skin. In order to achieve resistance to cold flow, preferred levels of skin adhesion and clean release, the amount and structure of the comonomers in the copolymer, the inherent viscosity of the copolymer, and the amount and type of adjuvant are selected such that the adhesive layer preferably has a compliance value of $2 \times 10^{-5}$ to $4 \times 10^{-5}$ cm$^2$/dyne. Compliance values can be determined using the Creep Compliance Procedure described in U.S. Pat. No. 4,737,559 (Kellen), the disclosure of which is incorporated herein by reference. Adhesive layers having compliance values outside of this range are also suitable. However, adhesive layers having substantially lower compliance values will generally be relatively stiff and have less than optimal adhesion to skin. Those having substantially higher compliance values will generally have less than optimal cold flow and might leave substantial residual adhesive when removed from the skin.

A transdermal delivery device of the invention also comprises a backing. The backing is flexible such that the device conforms to the skin. Suitable backing materials include conventional flexible backing materials used for pressure sensitive tapes, such as polyethylene, particularly low density polyethylene, linear low density polyethylene, metallocene polyethylenes, high density polyethylene, polypropylene, polyesters such as polyethylene terephthalate, randomly oriented nylon fibers, polypropylene, ethylene-vinyl acetate copolymer, polyurethane, natural fibers such as rayon and the like. Backings that are layered such as polyethylene-aluminum-polyethylene composites are also suitable. The backing should be substantially inert to the components of the adhesive layer.

Transdermal devices of the invention are preferably prepared by combining the copolymer, the adjuvant, the lauramine oxide (if any) and the testosterone with an organic solvent (e.g. ethyl acetate, methanol, acetone, 2-butanone, ethanol, isopropanol, toluene, alkanes and mixtures thereof) to provide a coating formulation. The components of the coating formulation are combined and shaken at high speed until a homogeneous formulation is obtained, then allowed to stand to dissipate air bubbles. The resulting coating formulation is knife coated onto a suitable release liner to provide a predetermined uniform thickness of coating formulation. Suitable release liners include conventional release liners comprising a known sheet material such as a polyester web, a polyethylene web, a polystyrene web, or a paper, coated with a suitable coating such as a fluoropolymer or other coating containing perfluorinated groups, silicone based coating or a hydrocarbon based coating such as polyethylene. The coated release liner is then dried to remove the organic solvent and then laminated to a backing using conventional methods. Depending on the drying parameters (e.g. oven temperature, dwell time in the oven, air flow through the oven) that are selected, some of the adjuvant may also be removed from the adhesive layer during drying. This loss may be compensated for by including additional adjuvant in the coating formulation. The amount of additional adjuvant needed may be easily determined by one skilled in the art by using conventional drying experiments (i.e. coating a formulation containing a known amount of adjuvant onto a release liner, drying the coated release liner under controlled conditions, determining the amount of adjuvant in the resulting coating, and calculating the amount of adjuvant that was lost during drying).

The examples set forth below are intended to illustrate the invention.

In Vitro Skin Penetration Test Method

The skin penetration data given in the examples below was obtained using the following test method. A diffusion cell is used with either hairless mouse skin or human cadaver skin.

When a transdermal delivery device is evaluated, the release liner is removed from a 2.0 cm$^2$ patch and the patch is applied to the skin and pressed to cause uniform contact with the skin. The resulting patch/skin laminate is placed patch side up across the orifice of the lower portion of the diffusion cell. The diffusion cell is assembled and the lower portion is filled with 10 mL of warm (32° C.) receptor fluid so that the receptor fluid is in contact with the skin. The receptor fluid is stirred using a magnetic stirrer. The sampling port is covered except when in use.

The cell is then placed in a constant temperature (32±2° C.) and humidity (50±10% relative humidity) chamber. The receptor fluid is stirred by means of a magnetic stirrer throughout the experiment to assure a uniform sample and a reduced diffusion barrier on the dermal side of the skin. The entire volume of receptor fluid is withdrawn at specified time intervals and immediately replaced with fresh fluid. The withdrawn fluid is filtered through a 0.45 $\mu$M filter then analyzed for testosterone using high performance liquid chromatography (Column: Supelcosil LC-18, 150×4.6 mm ID; Mobile Phase: 60% deaerated water, 40% HPLC grade acetonitrile; Flow rate: 2 mL/min; Detector: UV, 241 nm at 0.2 AUFS; Run Time: 5 minutes; Injection Volume: 20 $\mu$L). The cumulative amount of testosterone penetrating the skin and the flux rate are calculated.

The solubility of testosterone in various adjuvants was determined by a sequence of quantitative additions of testosterone to the respective adjuvant. The results of this evaluation are shown below.

| Adjuvant | Solubility mg/mL |
| --- | --- |
| Terpineol | 139.9 |
| Tetraglycol | 67.4 |
| Lauryl glycol | 40.0 |

The penetration of testosterone through hairless mouse skin from a saturated solution of testosterone in various adjuvants was determined using the skin penetration test method described above with a 2 mL portion of solution being used in place of the transdermal delivery device. The results of this evaluation are shown in the table below.

| Adjuvant | Cumulative Amount Penetrating ($\mu$g/mL) | |
| --- | --- | --- |
| | 24 hours | 48 hours |
| Terpineol | 1255 | 2842 |
| Tetraglycol | 34 | 95 |
| Lauryl glycol | 752 | 1771 |

Compliance Test Method

The compliance values given in the examples below were obtained using a modified version of the Creep Compliance Procedure described in U.S. Pat. No. 4,737,559 (Kellen). The release liner is removed from a sample of the material to be tested. The exposed surface is folded back on itself in the lengthwise direction to produce a "sandwich" configuration, i.e., backing/adhesive/backing. The "sandwiched" sample is passed through a laminator then two test samples of equal area are cut using a rectangular die. One test sample is centered on the stationary plate of a shear-creep rheometer with the long axis of the test sample centered on the short axis of the plate. The small, non-stationary plate of the shear-creep rheometer is centered over the first sample on the stationary plate such that the hook is facing up and toward the front of the rheometer. The second test sample is centered on the upper surface of the small, non-stationary plate matching the axial orientation of the first test sample. The large non-stationary plate is placed over the second test sample and the entire assembly is clamped into place. The end of the small, non-stationary plate that is opposite the end with the hook is connected to a chart recorder. A string is connected to the hook of the small, non-stationary plate and extended over the front pulley of the rheometer. A weight (e.g. 500 g) is attached to the free end of the string. The chart recorder is started and at the same time the weight is quickly released so that it hangs free. The weight is removed after exactly 3 minutes have elapsed. The displacement is read from the chart recorder. The compliance is then calculated using the equation:

$$J = 2\frac{AX}{hf}$$

where A is the area of one face of the test sample, h is the thickness of the adhesive mass (i.e., two times the thickness of the adhesive layer on the tested sample), X is the displacement and f is the force due to the mass attached to the string. Where A is expressed in cm$^2$, h in cm, X in cm and f in dynes, the compliance value is given in cm$^2$/dyne.

Preparation of Copolymer

The copolymers used in the examples that follow were prepared generally according to the methods described below. The inherent viscosity values which are reported were measured by conventional means using a Canon-Fenske # 50 viscometer in a water bath controlled at 27° C. to measure the flow time of 10 milliliters of a polymer solution (0.15 g of polymer per deciliter of ethyl acetate). The test procedure followed and the apparatus used are described in detail in "Textbook of Polymer Science", F. W. Billmeyer, Wiley-Interscience, Second Edition, 1971, pp 84–85.

Preparation of Isooctyl Acrylate/Acrylamide/Vinyl Acetate 73/7/20 Copolymer

A master batch was prepared by mixing isooctyl acrylate (1233.75 g), acrylamide (118.125 g), vinyl acetate (337.500 g) and 2,2'-azobis(2-methylbutanenitrile) (1.6875 g). A portion (225.475 g) of the master batch, ethyl acetate (257.7) and methanol (28.6 g) were placed in a 1 liter amber bottle. The mixture was deoxygenated by purging with nitrogen (1 L/min) for 2 minutes. The bottle was sealed and placed in a rotating water bath at 57° C. for 24 hours. The bottle was removed, opened, and then charged with ethyl acetate (214.8 g) and methanol (23.8 g). The contents were mixed until uniform (usually overnight). The percent solids of the resulting copolymer solution was 26.4. The inherent viscosity was 1.47 dl/g in ethyl acetate at 0.15 g/dl.

Preparation of "Dried" Copolymer

Dried copolymer is prepared by knife coating a solution of the copolymer at a thickness of about 9 mil (229 μM) onto a release liner. The coated release liner is oven dried at about 275° F. (135° C.) to remove the solvent and reduce the level of residual monomers. The dried copolymer is stripped from the release liner and stored until use.

EXAMPLE 1

Terpineol (442.31 g), lauramine oxide (25.00 g), testosterone, USP (75.00 g), copolymer (862.50 g of dried 73/7/20 isooctyl acrylate/acrylamide/vinyl acetate copolymer, iv=1.36 dl/g prior to drying), ethyl acetate (3202.00 g) and methanol (356.00 g) were combined in a 2 gallon (7.57 L) carboy container. The container was tightly covered then shaken for 14.5 hours on a platform shaker. The resulting formulation was allowed to stand until all entrapped air bubbles had dissipated then it was knife coated at a thickness of 31 mil (787 μM) onto a silicone release liner. The coated liner was oven dried for 4 minutes at 112° F. (44° C.), for 2 minutes at 185° F. (85° C.) and 2 minutes at 225° F. (107° C.). Assuming that 35 percent of the initial weight of terpineol evaporated off on drying, the resulting adhesive coating contained 23.0 percent terpineol, 2.0 percent lauramine oxide, 6.0 percent testosterone and 69.0 percent 73/7/20 isooctyl acrylate/acrylamide/vinyl acetate copolymer. The coated liner was then laminated to a backing (1109 Scotchpak™ tan, polyester film laminate, available from 3M Company, St. Paul, Minn., U.S.A.). The laminate was die cut into patches. The compliance was measured using the test method described above and found to be 2.342×10$^{-5}$ cm$^2$/dynes. The penetration through human cadaver and hairless mouse skin were determined using the test methods described above. The results are shown in Table 1 below where each value is the average of six independent determinations.

EXAMPLE 2

Terpineol (160.71 g), tetraglycol (133.93 g), lauryl glycol (130.81 g), testosterone, USP (48.75 g), copolymer (863.75 g of dried 73/7/20 isooctyl acrylate/acrylamide/vinyl acetate copolymer, iv=1.36 dl/g prior to drying), ethyl acetate (3202.00 g) and methanol (356.00 g) were combined in a 2 gallon (7.57 L) carboy container. The container was tightly covered then shaken for 14.5 hours on a platform shaker. The resulting formulation was allowed to stand until all entrapped air bubbles had dissipated then it was knife coated at a thickness of 30 mil (762 μM) onto a silicone release liner. The coated liner was oven dried for 4 minutes at 111° F. (44° C.), for 2 minutes at 184° F. (84° C.) and 2 minutes at 225° F. (107° C.). Assuming that 30 percent of the initial weight of terpineol, 16% of the initial weight of tetraglycol and 14% of the initial weight of lauryl glycol evaporated off on drying, the resulting adhesive coating contained 9.0 percent terpineol, 9.0 percent tetraglycol, 9.0 percent lauryl glycol, 3.9 percent testosterone and 69.1 percent 73/7/20 isooctyl acrylate/acrylamide/vinyl acetate copolymer. The coated liner was then laminated to a backing (1109 Scotchpak™ tan, polyester film laminate, available from 3M Company, St. Paul, Minn., U.S.A.). The laminate was die cut into patches. The compliance was measured using the test method described above and found to be 2.477×10$^{-5}$ cm$^2$/dynes. The penetration through human cadaver and hairless mouse skin were determined using the test methods described above. The results are shown in Table 1 below where each value is the average of six independent determinations.

EXAMPLE 3

Tetraglycol (238.10 g), lauryl glycol (116.28 g), testosterone, USP (36.25 g), copolymer (913.75 g of dried 73/7/20 isooctyl acrylate/acrylamide/vinyl acetate copolymer, iv=1.36 dl/g prior to drying), ethyl acetate (3202.00 g) and methanol (356.00 g) were combined in a 2 gallon (7.57 L) carboy container. The container was tightly covered then shaken for 14.5 hours on a platform shaker. The resulting formulation was allowed to stand until all entrapped air bubbles had dissipated then it was knife coated at a thickness of 30 mil (762 µM) onto a silicone release liner. The coated liner was oven dried for 4 minutes at 111° F. (44° C.), for 2 minutes at 185° F. (85° C.) and 2 minutes at 226° F. (108° C.). Assuming that 16% of the initial weight of tetraglycol and 14% of the initial weight of lauryl glycol evaporated off on drying, the resulting adhesive coating contained 16.0 percent tetraglycol, 8.0 percent lauryl glycol, 2.9 percent testosterone and 73.1 percent 73/7/20 isooctyl acrylate/acrylamide/vinyl acetate copolymer. The coated liner was then laminated to a backing (1109 Scotchpak™ tan, polyester film laminate, available from 3M Company, St. Paul, Minn., U.S.A.). The laminate was die cut into patches. The compliance was measured using the test method described above and found to be $3.795 \times 10^{-5}$ cm²/dyne. The penetration through human cadaver and hairless mouse skin were determined using the test methods described above. The results are shown in Table 1 below where each value is the average of six independent determinations.

TABLE 1

| Example Number | Cumulative Amount Penetrating in 24 Hours (µg/cm²) | |
|---|---|---|
| | Hairless Mouse Skin | Human Cadaver Skin |
| 1 | 523 | 174 |
| 2 | 198 | 113 |
| 3 | 148 | 87 |

EXAMPLES 4–17

Using the general method of Example 1, a series of transdermal delivery devices in which the amount of testosterone and the amount and choice of adjuvant were varied was prepared. In all instances the copolymer used was 73/7/20 isooctyl acrylate/acrylamide/vinyl acetate. The weight percent of testosterone, weight percent and identity of adjuvant, weight percent of lauramine oxide (if used) and the cumulative skin penetration through hairless mouse skin are given in Table 2 below. The balance of each formulation to 100 weight percent was copolymer. The abbreviations T, TP, TG, LG and LAO are used for testosterone, terpineol, tetraglycol, lauryl glycol and lauramine oxide respectively.

TABLE 2

| Example Number | % T | Adjuvant | Cumulative Amount Penetrating (µg/cm²) | |
|---|---|---|---|---|
| | | | 24 hours | 48 hours |
| 4 | 5.9 | 30% TP | 286 | 473 |
| 5 | 6.3 | 35% TP; 3% LAO | 575 | 686 |
| 6 | 3.6 | 30% TP; 3% LAO | 484 | Not run |
| 7 | 4.3 | 10% TP; 10% TG; 10% LG | 320 | 447 |
| 8 | 5.2 | 20% TP; 10% TG | 320 | 501 |
| 9 | 5.1 | 20% TP; 10% LG | 252 | 436 |
| 10 | 3.8 | 30% TG | 120 | 238 |
| 11 | 4.0 | 30% TG | 179 | 309 |
| 12 | 3.3 | 30% LG | 151 | 272 |
| 13 | 3.5 | 30% LG | 185 | 293 |
| 14 | 3.4 | 30% LG; 3% LAO | 362 | Not run |
| 15 | 3.9 | 30% TG; 3% LAO | 285 | Not run |

TABLE 2-continued

| Example Number | % T | Adjuvant | Cumulative Amount Penetrating (µg/cm²) | |
|---|---|---|---|---|
| | | | 24 hours | 48 hours |
| 16 | 4.4 | 10% TP; 10% TG; 10% LG; 3% LAO | 420 | Not run |
| 17 | 3.7 | 15% TG; 15% LG | 262 | 367 |

EXAMPLES 18–23

Using the general method of Example 1, a series of transdermal delivery devices in which the amount of testosterone and the amount and choice of adjuvant were varied was prepared. In all instances the copolymer used was 73/7/20 isooctyl acrylate/acrylamide/vinyl acetate. The weight percent of testosterone, weight percent and identity of adjuvant, and the cumulative skin penetration through human cadaver skin are given in Table 3 below. The balance of each formulation to 100 weight percent was copolymer. The abbreviations T, TP, TG, and LG are used for testosterone, terpineol, tetraglycol and lauryl glycol respectively.

TABLE 3

| Example Number | % T | Adjuvant | Cumulative Amount Penetrating (µg/cm²) | |
|---|---|---|---|---|
| | | | 24 hours | 48 hours |
| 18 | 6.1 | 30% TP | 153 | 252 |
| 19 | 4.0 | 30% TG | 255 | 336 |
| 20 | 3.4 | 30% LG | 281 | 346 |
| 21 | 5.1 | 15% TP; 15% TG | 243 | 347 |
| 22 | 4.8 | 15% TP; 15% LG | 116 | 192 |
| 23 | 3.8 | 15% TG; 15% LG | 223 | 284 |

EXAMPLES 24–28

Using the general method of Example 1, a series of transdermal delivery devices in which the amount of testosterone and the amount and choice of adjuvant were varied was prepared. In all instances the copolymer used was 73/7/20 isooctyl acrylate/acrylamide/vinyl acetate. The weight percent of testosterone, weight percent and identity of adjuvant, and the average flux through human cadaver skin are given in Table 4 below. The balance of each formulation to 100 weight percent was copolymer. The abbreviations T, TP, TG, and LG are used for testosterone, terpineol, tetraglycol and lauryl glycol respectively. Each flux value is the average of 3 independent determinations.

TABLE 4

| Example Number | % T | Adjuvant | Average Flux (µg/cm²/hr) |
|---|---|---|---|
| 24 | 8 | 30% TP | 3.37 |
| 25 | 4.75 | 15% TP; 7.5% TG; 7.5% LG | 3.82 |
| 26 | 4.33 | 10% TP; 10% TG; 10% LG | 5.31 |
| 27 | 3.34 | 30% LG | 4.15 |
| 28 | 3.68 | 20% TG; 10% LG | 5.21 |

EXAMPLE 29

Terpineol (3.5294 g), N,N-cocodiethanolamide (3.0011), testosterone (0.9801 g), copolymer (13.020 g of dried 73/7/

20 isooctyl acrylate/acrylamide/vinyl acetate copolymer, iv=1.36 dl/g prior to drying), ethyl acetate (47.747 g) and methanol (9.259 g) were combined in a 4 ounce (118 ml) glass jar. The jar was tightly covered then shaken on a roller mixer for 12 hours. The resulting formulation was sonicated to remove bubbles. The formulation was knife coated at a thickness of 30 mils (762 $\mu$M) onto a silicon release liner. The coated liner was allowed to air dry at ambient temperature for 1.5 minutes then it was oven dried at 110° F. (43° C.) for 10 minutes. Assuming that 15 percent of the initial weight of terpineol evaporated off on drying, the resulting adhesive coating contained 15.0 percent terpineol, 15.0 percent cocamide DEA, 4.9 percent testosterone and 65.1 percent 73/7/20 isooctyl acrylate/acrylamide/vinyl acetate copolymer. The coated liner was laminated to a backing (1014 Scotchpak™). The laminate was die cut into patches. The penetration through human cadaver skin and hairless mouse skin was determined using the test method described above. The results are shown in Table 5 below where each value is the average of four independent determinations.

EXAMPLES 30–31

Using the general method of Example 29, a series of transdermal devices in which the amount of testosterone and the amount and choice of adjuvant were varied was prepared. In all instances the copolymer used was 73/7/20 isooctyl acrylate/acrylamide/vinyl acetate. The weight percent of testosterone, weight percent and identity of adjuvant, and the cumulative skin penetration through human cadaver skin and hairless mouse skin are given in Table 5 below. The balance of each formulation to 100 weight percent was copolymer. The abbreviations T, TP, CDEA, GLY and LPCA are used for testosterone, terpineol, N,N-cocodiethanolamide, glycerol and lauryl pyrrolidone-5-carboxylate respectively.

TABLE 5

| Example Number | % T | Adjuvant | Cumulative Amount Penetrating in 24 hours ($\mu$g/cm$^2$) | |
| --- | --- | --- | --- | --- |
| | | | Human Cadaver | Hairless Mouse |
| 29 | 4.9 | 15% TP; 15% CDEA | 346 | 463 |
| 30 | 3.0 | 10% TP; 10% GLY 10% LPCA | 120 | 156 |
| 31 | 5.5 | 20% TP; 5% GLY 5% LPCA | 281 | 370 |

EXAMPLE 32

Terpineol (1.9392g), lauryl pyrrolidone-5-carboxylate (0.270 g), glycerol (0.270 g), testosterone (0.3001 g), copolymer (3.900 g of dried 72/8/20 isooctyl acrylate/acrylamide/vinyl acetate copolymer, iv=1.47 dl/g prior to drying), ethyl acetate (23.0219 g) and methanol (2.569 g) were combined in a 11 dram (41 ml) glass vial. The vial was tightly covered then shaken on a platform shaker for 12 hours. The formulation was knife coated at a thickness of 44 mils ( 1118 $\mu$M) onto a silicon release liner. The coated liner was allowed to air dry at ambient temperature for 2 minutes then it was oven dried at 110° F. (43° C.) for 4 minutes, at 185° F. (85° C.) for 2 minutes, and at 225° F. (107° C.) for 2 minutes. Assuming t percent of the initial weight of terpineol evaporated off on drying, the resulting adhesive coating contained 21.0 percent terpineol, 4.5 percent lauryl pyrrolidone-5-carboxylate, 4.5% glycerol, 5.0 percent testosterone and 65.0 percent 72/8/20 isooctyl acrylate/acrylamide/vinyl acetate copolymer. The coated liner was laminated to a backing (1012 Scotchpak™ transparent, heat sealable, polyester film laminate). The laminate was die cut into patches. The penetration through hairless mouse skin was determined using the test method described above. The results are shown in Table 6 below where each value is the average of four independent determinations.

EXAMPLES 33–37

Using the general method of Example 32, a series of transdermal devices in which the amount of testosterone and the amount and choice of adjuvant were varied was prepared. In all instances the copolymer used was 72/8/20 isooctyl acrylate/acrylamide/vinyl acetate. The weight percent of testosterone, weight percent and identity of adjuvant, and the cumulative skin penetration through hairless mouse skin are given in Table 6 below. The balance of each formulation to 100 weight percent was copolymer. The abbreviations T, TP, GLY and LPCA are used for testosterone, terpineol, glycerol and lauryl pyrrolidone-5-carboxylate respectively.

TABLE 6

| Example Number | % T | Adjuvant | Cumulative Amount Penetrating in 24 hours ($\mu$g/cm$^2$) |
| --- | --- | --- | --- |
| 32 | 5.0 | 21% TP; 4.5% GLY 4.5% LPCA | 332 |
| 33 | 4.5 | 21% TP; 4.5% GLY 4.5% LPCA | 293 |
| 34 | 4.0 | 21% TP; 4.5% GLY 4.5% LPCA | 230 |
| 35 | 4.5 | 23.25% TP; 4.% GLY 2.25% LPCA | 231 |
| 36 | 5.0 | 23.25% TP; 4.5% GLY 2.25% LPCA | 243 |
| 37 | 5.5 | 23.25% TP; 4.5% GLY 2.25% LPCA | 315 |

EXAMPLE 38

Terpineol (1.1071 g), lauryl alcohol (0.2020), lauryl pyrrolidone-5-carboxylate (0.120 g), glycerol (0.180 g), testosterone (0.1923 g), copolymer (2.8000 g of dried 73/7/20 isooctyl acrylate/acrylamide/vinyl acetate copolymer, iv=1.36 dl/g prior to drying), ethyl acetate (10.2462 g) and methanol (1.1447 g) were combined in a 6 dram (22 ml) glass vial. The vial was tightly covered then shaken on a platform a platform shaker for 12 hours. The formulation was knife coated at a thickness of 30 mils (762 $\mu$M) onto a silicon release liner. The coated liner was allowed to air dry at ambient temperature for a minimum of 3 to 4 minutes then it was oven dried at 110° F. (43° C.) for 4 minutes, at 185° F. (85° C.) for 2 minutes, and 225° F. (107° C.) for 2 minutes. Assuming that 35 percent of the initial weight of terpineol and 5 percent of the initial weight of lauryl alcohol evaporated off on drying, the resulting adhesive coating contained 17.1 percent terpineol, 4.6 percent lauryl alcohol, 2.8 percent lauryl pyrrolidone-5-carboxylate, 4.3% glycerol, 4.6 percent testosterone and 65.6 percent 73/7/20 isooctyl acrylate/acrylamide/vinyl acetate copolymer. The coated liner was laminated to a backing (1012 Scotchpak™ transparent, heat sealable, polyester film laminate). The laminate was die cut into patches. The penetration through hairless mouse skin was determined using the test method described above. The results are shown in Table 7 below where each value is the average of four independent determinations.

EXAMPLES 39–40

Using the general method of Example 38, a series of transdermal devices in which the amount of testosterone and the amount and choice of adjuvant were varied was prepared. In all instances the copolymer used was 73/7/20 isooctyl acrylate/acrylamide/vinyl acetate. The weight percent of testosterone, weight percent and identity of adjuvant, and the cumulative skin penetration through hairless mouse skin are given in Table 7 below. The balance of each formulation to 100 weight percent was copolymer. The abbreviations T, TP, GLY, LALC and LPCA are used for testosterone, terpineol, glycerol, lauryl alcohol and lauryl pyrrolidone-5-carboxylate respectively.

TABLE 7

| Example Number | % T | Adjuvant | Cumulative Amount Penetrating in 24 hours ($\mu g/cm^2$) |
|---|---|---|---|
| 38 | 4.6 | 17.1% TP; 4.3% GLY 4.6% LALC; 2.8% LPCA | 341 |
| 39 | 4.3 | 15.8% TP; 4.5% GLY 8.6% LALC | 306 |
| 40 | 5.2 | 18.8% TP; 9.4% LALC | 320 |

EXAMPLE 41

Using the general method of Example 38, transdermal delivery devices in which the adhesive coating contained 18.0 percent terpineol, 4.5 percent lauryl alcohol, 4.5 percent glycerol, 3.0 percent lauryl pyrrolidone-5-carboxylate, 4.8 percent testosterone and 65.2 percent 73/7/20 isooctyl acrylate/acrylamide/vinyl acetate were prepared. Penetration through hairless mouse skin and through three different lots of human cadaver skin was determined using the test method described above. The results are shown in Table 8 below where each entry is the average of four independent determinations.

EXAMPLE 42

Using the general method of Example 38, transdermal delivery devices in which the adhesive coating contained 19.8 percent terpineol, 9.9 percent lauryl alcohol, 5.5 percent testosterone and 64.8 percent 73/7/20 isooctyl acrylate/acrylamide/vinyl acetate were prepared. Penetration through hairless mouse skin and through three different lots of human cadaver skin was determined using the test method described above. The results are shown in Table 8 below where each entry is the average of four independent determinations.

TABLE 8

| | Cumulative Amount Penetrating in 24 hours ($\mu g/cm^2$) | |
|---|---|---|
| Skin type | Example 41 | Example 42 |
| Human cadaver (lot 1) | 280 | 256 |
| Human cadaver (lot 2) | 330 | 270 |
| Human cadaver (lot 3) | 136 | 116 |
| Hairless mouse | 411 | 337 |

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the exact details of the compositions and structures described herein, but rather by the structures and compositions described by the language of the claims, and their equivalents.

What is claimed is:

1. A device for the transdermal delivery of testosterone comprising a backing having an adhesive layer adhered to one surface of the backing, said adhesive layer comprising:
    (a) a pressure sensitive skin adhesive;
    (b) a therapeutically effective amount of testosterone; and
    (c) a delivery enhancing adjuvant comprising a terpene.
2. The device of claim 1 wherein the delivery enhancing adjuvant comprises a terpene and a fatty acid derivative.
3. The device of claim 1 wherein the terpene comprises pinene, d-limonene, carene, terpineol, terpinen-4-ol, carveol, carvone, pulegone, piperitone, menthone, menthol, neomenthol, thymol, camphor, borneol, citral, ionone, and cineole, or a combination thereof.
4. The device of claim 1 wherein the terpene comprises α-terpineol.
5. The device of claim 2 wherein the fatty acid derivative comprises a derivative of a $C_{6-20}$ fatty acid.
6. The device of claim 2 wherein the fatty acid derivative is a derivative of lauric acid.
7. The device of claim 2 wherein the fatty acid derivative comprises lauroglycol, lauramide DEA, lauryl alcohol, lauryl pyrrolidone-5-carboxylate, lauramine oxide, or a combination thereof.
8. The device of claim 1 wherein the delivery enhancing adjuvant further comprises glycerol.
9. The device of claim 1 wherein the delivery enhancing adjuvant comprises a terpene, a fatty acid derivative, and glycerol.
10. The device of claim 1 wherein the delivery enhancing adjuvant comprises terpineol and lauryl alcohol.
11. The device of claim 10 wherein the delivery enhancing adjuvant further comprises lauryl pyrrolidone-5-carboxylate and glycerol.
12. The device of claim 1 wherein the testosterone is dissolved in the adhesive layer.
13. A device for the transdermal delivery of testosterone comprising a backing having an adhesive layer adhered to one surface of the backing, said adhesive layer comprising:
    (a) a pressure sensitive skin adhesive that comprises a copolymer of
        (i) one or more A monomers selected from the group consisting of alkyl (meth)acrylates containing 4 to 10 carbons in the alkyl group and
        (ii) one or more ethylenically unsaturated B monomers containing a functional group selected from the group consisting of carboxylic acid, sulfonamide, urea, carbamate, carboxamide, hydroxy, amino, oxy, oxo and cyano;
    (b) a therapeutically effective amount of testosterone; and
    (c) a delivery enhancing adjuvant comprising a terpene.
14. The device of claim 13 wherein the one or more A monomers are selected from the group consisting of isooctyl acrylate, 2-ethylhexyl acrylate, butyl acrylate, and cyclohexyl acrylate.
15. The device of claim 13 wherein the one or more B monomers are selected from the group consisting of acrylic acid, methacrylic acid, acrylamide, vinyl acetate and methacrylamide.
16. The device of claim 13 wherein the copolymer further comprises one or more substantially linear macromonomers copolymerizable with the A and B monomers.

17. The device of claim 13 wherein the copolymer is a copolymer of isooctyl acrylate, acrylamide, and vinyl acetate.

18. A device for the transdermal delivery of testosterone comprising a backing having an adhesive layer adhered to one surface of the backing, said adhesive layer comprising
   (a) a pressure sensitive skin adhesive comprising a copolymer of isooctyl acrylate, acrylamide, and vinyl acetate;
   (b) a therapeutically effective amount of testosterone;
   (c) α-terpineol;
   (d) lauryl alcohol;
   (e) lauryl pyrrolidone-5-carboxylate; and
   (f) glycerol.

19. A method of treating a condition associated with testosterone deficiency in a mammal comprising the steps of
   (a) providing a device according to claim 1;
   (b) applying the device to the skin of a mammal; and
   (c) allowing the device to remain on the skin for a time sufficient to establish or maintain a therapeutically effective blood level of testosterone in the mammal.

20. A device for the transdermal delivery of testosterone comprising a backing having an adhesive layer adhered to one surface of the backing, said adhesive layer comprising:
   (a) a pressure sensitive skin adhesive that comprises a copolymer of
      (i) an A monomer comprising isooctyl acrylate and
      (ii) one or more ethylenically unsaturated B monomers containing a functional group selected from the group consisting of carboxylic acid, sulfonamide, urea, carbamate, carboxamide, hydroxy, amino, oxy, oxo and cyano;
   (b) a therapeutically effective amount of testosterone; and
   (c) a delivery enhancing adjuvant comprising a terpene.

* * * * *

UNITED STATES PATENT AND TRADEMARK OFFICE
CERTIFICATE OF CORRECTION

PATENT NO.: 6,132,760
DATED: October 17, 2000
INVENTOR(S): John C. Hendenstrom, Michael L. Husberg, Shari L. Wilking Myszka, and Matthew T. Scholz It is certified that error appears in the above-identified patent and that said Letters Patent is hereby corrected as shown below:

On the Title Page, item [75], please delete "Shari L. Wilking" and insert --Shari L. Wilking Myszka--.

Claim 1, line 13, delete the words "a terpene" and insert --terpineol--.

Claim 2, line 15, delete the words "a terpene" and insert --terpineol--.

Claim 3, delete.

Claim 4, line 20, delete the word "terpene" and insert --terpineol--.

Claim 9, line 33, delete the words "a terpene" and insert --terpineol--.

Claim 13, line 56, delete the words "a terpene" and insert --terpineol--.

Signed and Sealed this

Twenty-second Day of May, 2001

*Attest:*

NICHOLAS P. GODICI

*Attesting Officer*  *Acting Director of the United States Patent and Trademark Office*